(12) United States Patent
Kim et al.

(10) Patent No.: US 7,667,843 B2
(45) Date of Patent: Feb. 23, 2010

(54) METHOD OF EVALUATING SENSITIVITY GRADE OF INTERIOR MATERIAL USED IN VEHICLES

(75) Inventors: Jong Myung Kim, Gyeonggi-do (KR); Young Jin Lee, Gyeonggi-do (KR); Won Jin Seo, Gyeonggi-do (KR); Yun Seok Kim, Yongin-Si (KR); Yeong Nam Hwang, Gyeongsangbuk-do (KR); Won Jun Kim, Gyeongsangbuk-do (KR)

(73) Assignees: Hyundai Motor Company, Seoul (KR); Kia Motors Corporation, Seoul (KR); Kolon Industries Inc., Incheon (KR)

( * ) Notice: Subject to any disclaimer, the term of this patent is extended or adjusted under 35 U.S.C. 154(b) by 0 days.

(21) Appl. No.: 12/150,978

(22) Filed: May 2, 2008

(65) Prior Publication Data

US 2009/0153863 A1    Jun. 18, 2009

(30) Foreign Application Priority Data

Dec. 12, 2007    (KR) ...................... 10-2007-0129230

(51) Int. Cl.
*G01J 3/46* (2006.01)
(52) U.S. Cl. ........................ 356/402; 356/238.1; 702/81
(58) Field of Classification Search ............... 356/238.1; 702/81
See application file for complete search history.

(56) References Cited

U.S. PATENT DOCUMENTS 6,577,971 B2 *    6/2003    Aitken et al. .................. 702/81

FOREIGN PATENT DOCUMENTS

| JP | 10-274577 | 10/1998 |
|---|---|---|
| JP | 2003-315274 | 11/2003 |
| KR | 10-2004-0110657 | 12/2004 |
| KR | 10-2007-0041806 | 4/2007 |

* cited by examiner

*Primary Examiner*—Gregory J Toatley, Jr.
*Assistant Examiner*—Abdullahi Nur
(74) *Attorney, Agent, or Firm*—Edwards Angell Palmer & Dodge LLP; Peter F. Corless

(57) ABSTRACT

A method of evaluating the sensitivity grade of an interior material used in vehicles comprises: evaluating sensitivity properties of an interior material before providing noise factors; evaluating sensitivity properties of the interior material after providing noise factors; averaging each of the sensitivity properties evaluated before the provision of noise factors and after the provision of noise factors to obtain the average value (safety factor) of each of the sensitivity properties; comparing the average value of each of the sensitivity properties with a preset target value of each of the sensitivity properties to compute a target value achievement level of each of the sensitivity properties; and determining the sensitivity grade of the interior material based on the sensitivity property with the lowest target value achievement level. By providing an objective standard to evaluate sensitivity properties of an interior material used in vehicles, the present method(s) eliminates the difficulty in communication between customers and manufactures and quality control regarding the sensitivity grade of interior materials used in vehicles.

4 Claims, No Drawings

METHOD OF EVALUATING SENSITIVITY GRADE OF INTERIOR MATERIAL USED IN VEHICLES

CROSS-REFERENCE TO RELATED APPLICATION

This application claims under 35 U.S.C. §119(a) the benefit of Korean Patent Application No. 10-2007-0129230 filed on Dec. 12, 2007, the entire contents of which are incorporated herein by reference.

BACKGROUND (a) Technical Field

The present invention relates to a method of evaluating the sensitivity grade of an interior material used in vehicles for providing an objective standard to evaluate sensitivity properties of an interior material used in vehicles.

(a) Background Art

Artificial leather, which comprises a nonwoven fabric in which microfibers are interlocked three-dimensionally and elastic polymers impregnated in the nonwoven fabric, is widely used as seat covers or interior materials of vehicles including automobiles, airplanes, trains, ships, and the like because of its excellent touch, lighting effect, drape, etc., soft texture similar to that of natural leather, and characteristic appearance.

As disclosed in Korean Patent No. 0323637, for example, artificial leather can be prepared by buffing and dyeing an artificial leather sheet substrate comprising a nonwoven fabric composed of entangled bundles of polyamide-based microfibers having a filament fineness of 0.1 decitex or less and elastic polymers impregnated in the nonwoven fabric.

Of recent, artificial leather is recognized as high sensitivity material and its use in interior materials of vehicles is increasing. In this regard, aesthetic factors such as subdued lighting effect are considered important.

Artificial leather provides excellent touch and look because of the microfiber texture. Different feelings can be provided depending on viewing angles. Further, since the elastic polymers impregnated in the nonwoven fabric provide structural stability and elasticity, it is well-suited as interior material used in vehicles.

However, to date, there has been no systematic and objective standard for evaluation of sensitivity properties of the interior material used in vehicles, such as dynamic elongation, permanent compression set, color development, dynamic friction constant and color variation. As such, there is difficulty in communication between customers and manufactures and quality control regarding the sensitivity grade of interior materials used in vehicles.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with the prior art.

One of the objects of the present invention is to provide a method of evaluating systematically and objectively the sensitivity grade of an interior material used in vehicles.

In one aspect, the present invention provides a method of evaluating the sensitivity grade of an interior material used in vehicles comprising the steps of: (i) evaluating sensitivity properties of an interior material, wherein microfibers having a fineness of 0.001 to 0.3 denier are interlocked in a nonwoven, elastic polymers are impregnated therein, and the microfibers are standing on the surface to form fluffs, before irradiating the interior material with xenon arc to provide noise factors; (ii) evaluating sensitivity properties of the interior material after irradiating the interior material with xenon arc having a wavelength in the range from 300 to 400 nm to provide noise factors; (iii) averaging each of the sensitivity properties evaluated before the provision of noise factors and after the provision of noise factors to obtain the average value (safety factor) of each of the sensitivity properties; (iv) comparing the average value (safety factor) of each of the sensitivity properties with a predetermined target value of each of the sensitivity properties to compute a target value achievement level of each of the sensitivity properties; and (v) determining the sensitivity grade of the interior material based on the sensitivity property with the lowest target value achievement level.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like.

Other features of the invention are discussed infra.

DETAILED DESCRIPTION

Reference will now be made in detail to the preferred embodiments of the present invention.

The method of evaluating the sensitivity grade of an interior material used in vehicles according to the present invention is characterized by evaluating sensitivity properties of an interior material before providing noise factors and after providing noise factors, computing average value (safety factor) of each of the sensitivity properties, comparing the average value of each of the sensitivity properties with a predetermined target value of each of the sensitivity properties to compute a target value achievement level of each of the sensitivity properties, and determining the sensitivity grade of the interior material based on the sensitivity property with the lowest target value achievement level.

Artificial leather as vehicle interior material has a structure in which microfibers having a fineness of 0.001 to 0.3 denier are interlocked in a nonwoven, elastic polymers are impregnated therein, and the microfibers are standing on the surface to form fluffs.

Examples of the elastic polymers may include a polyurethane resin, a polyurea resin, etc. A polyurethane resin is preferred in light of processability.

The microfiber may be one commonly used in the art and is not particularly limited. For example, polyamide fiber, polyester fiber, etc. may be used.

The fineness of the microfiber is maintained from 0.001 to 0.3 denier. A fineness lower than 0.001 denier may result in reduced strength of the interior material, and a fineness higher than 0.3 denier may result in degraded touch and lighting effect of the interior material.

Preferably, the method of the present invention comprises the following five steps.

First, each of the sensitivity properties of the interior material is evaluated before irradiating the interior material with xenon arc to provide noise factors. Here, the sensitivity properties include color development, color variation, dynamic elongation, permanent compression set and dynamic friction constant.

Second, each of the sensitivity properties of the interior material is evaluated after irradiating the interior material with xenon arc having a wavelength in the range from 300 to 400 nm to provide noise factors. A wavelength shorter than 300 nm makes too stringent a condition to be practicable, whereas a wavelength longer than 400 nm makes too mild a condition to provide discrimination between samples. Hence, the aforesaid range is preferred.

The xenon arc is irradiated with an intensity from 20 to 150 $MJ/m^2$, preferably from 42 to 126 $MJ/m^2$, more preferably 84 $MJ/m^2$. An intensity below 20 $MJ/m^2$ results in insignificant noise effect, with little difference in the sensitivity properties before and after providing noise factors. On the other hand, an intensity exceeding 150 $MJ/m^2$ results in too strong noise effect, making the comparison of the sensitivity properties after the provision of noise factors impossible. Hence, the aforesaid range is preferred.

Third, each of the sensitivity properties of the interior material evaluated before and after the provision of noise factors is averaged to compute the average value (safety factor) of each of the sensitivity properties.

Fourth, the average value of each of the sensitivity properties is compared with a predetermined target value of each of the sensitivity properties to compute a target value achievement level of each of the sensitivity properties. The target value of each of the sensitivity properties is determined at random depending on experiences or market needs.

Fifth, the sensitivity grade of the interior material is determined based on the sensitivity property with the lowest target value achievement level.

For example, the sensitivity grade may be determined as follows: 1st grade is given when the sensitivity property with the lowest target value achievement level is 99% of the target value achievement level; 2nd grade is given when the sensitivity property with the lowest target value achievement level is from 90% to 99% of the target value achievement level; 3rd grade is given when the sensitivity property with the lowest target value achievement level is from 80% to 90% of the target value achievement level; 4th grade is given when the sensitivity property with the lowest target value achievement level is from 70% to 80% of the target value achievement level: and 5th grade is given when the sensitivity property with the lowest target value achievement level is below 70% of the target value achievement level.

The color development is measured using a computer color matching apparatus. It is the average value of the lightness $L_1$ along the standing direction of the fluffs of the interior material and the lightness $L_2$ in the opposite direction.

The color variation ($\Delta E$) is also measured using a computer color matching apparatus. It is the variation between the color value $E_1$ along the standing direction of the fluffs of the interior material and the color value $E_2$ in the opposite direction.

The dynamic friction constant is measured in the opposite direction of the standing direction of the fluffs of the interior material.

The dynamic elongation is measured as follows. A load is applied to a sample mounted on a tensile tester at constant speed from the minimum load of 0 kgf to the maximum load of 8 kgf. Then, the load is decreased from the maximum load to the minimum load at constant speed. After repeating 100 cycles, the elongation at the 100th application of the maximum load is the dynamic elongation. The constant speed may be in the range from 100 mm/min to 300 mm/min, as commonly used in the art. In a preferred embodiment, the constant speed may be maintained at 200 mm/min because the measurement result varies depending on the speed. The minimum load and the maximum load can be determined taking into consideration the load applied on the interior material, for example, during installation. Preferably, the load is maintained in the range from 0 to 8 kgf. The minimum load 0 kgf is the state with no load applied. The maximum load 8 kgf corresponds to the load applied during the installation of the interior material.

The permanent compression set is measured as follows. A load is applied to a sample mounted on a tensile tester at constant speed from the minimum load of 0 kgf to the maximum load of 8 kgf. Then, the load is decreased from the maximum load to the minimum load at constant speed. After repeating 100 cycles, the elongation at the minimum load after the 100th application of the maximum load is the permanent compression set.

The aforesaid sensitivity properties are evaluated as follows.

(1) Color Value $E_1$ Along the Standing Direction of the Fluffs

The surface of the sample of the interior material is slightly hand-stroked 3 times along the standing direction of the fluffs. After measurement of lightness $L_1$, color way $a_1$ and color way $b_1$ using a computer color matching apparatus, the color value $E_1$ along the standing direction of the fluffs is computed by the following equation.

$$E_1 = \sqrt{(L_1)^2 + (a_1)^2 + (b_1)^2}$$

(2) Color Value ($E_2$) Color Value $E_2$ in the Opposite Direction of the Standing Direction of the Fluffs The surface of the sample of the interior material is slightly hand-stroked 3 times in the opposite direction of the standing direction of the fluffs. After measurement of lightness $L_2$, color way $a_2$ and color way $b_2$ using a computer color matching apparatus, the color value $E_2$ in the opposite direction of the standing direction of the fluffs is computed by the following equation.

$$E_2 = \sqrt{(L_2)^2 + (a_2)^2 + (b_2)^2}$$

(3) Color variation ($\Delta E$) between $E_1$ and $E_2$

The color variation ($\Delta E$) is computed by the following equation from the color value $E_1$ along the standing direction of the fluffs and the color value $E_2$ in the opposite direction.

$$\Delta E = \sqrt{(L_1 - L_2)^2 + (a_1 - a_2)^2 + (b_1 - b_2)^2}$$

(4) Dynamic Elongation and Permanent Compression Set

A sample of size 50 mm×250 mm is mounted on a tensile tester with a gauge length of 130 mm. After applying a load at constant speed with 200 m/min of x-head speed from the minimum load of 0 kgf to the maximum load of 8 kgf, the load is decreased from the maximum load to the minimum load at constant speed. After repeating 100 cycles, the elongation at the 100th application of the maximum load (8 kgf) is determined as the dynamic elongation, and the elongation at the minimum load after the 100th application of the maximum load (0 kgf) is determined as the permanent compression set.

(5) Thickness and Fineness (Denier) of Microfiber

A sample of the interior material is taken and, after a preparation process such as gold coating, the cross-section of the sample is taken using a scanning electron microscope (SEM). The diameter of a single strand of the microfiber is measured from the micrograph, and the fineness is computed by the following equation.

$$\text{Fineness(denier)} = 9\pi D^2 \rho / 4000$$

where π is the ratio of the circumference of a circle to its diameter, D is the cross-sectional diameter of the microfiber (μm), and ρ is the density of the microfiber (g/cm$^3$). For reference, the density of nylon and polyethylene terephthalate is 1.14 and 1.38, respectively.

By providing an objective standard to evaluate sensitivity properties of an interior material used in vehicles, the present invention eliminates the difficulty in communication between customers and manufactures and quality control regarding the sensitivity grade of interior materials used in vehicles.

The present invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method of evaluating the sensitivity grade of an interior material used in vehicles comprising the steps of:
   (i) evaluating sensitivity properties of an interior material, wherein microfibers having a fineness of 0.001 to 0.3 denier are interlocked in a nonwoven, elastic polymers are impregnated therein, and the microfibers are standing on the surface to form fluffs, before irradiating the interior material with xenon arc to provide noise factors;
   (ii) irradiating the interior material with xenon arc having a wavelength in the range from 300 to 400 nm to provide noise factors, and after irradiating evaluating sensitivity properties of the interior material;
   (iii) averaging each of the sensitivity properties evaluated before the provision of noise factors and after the provision of noise factors to obtain the average value (safety factor) of each of the sensitivity properties;
   (iv) comparing the average value (safety factor) of each of the sensitivity properties with a predetermined target value of each of the sensitivity properties to compute a target value achievement level of each of the sensitivity properties; and
   (v) determining the sensitivity grade of the interior material based on the sensitivity property with the lowest target value achievement level.

2. The method of evaluating the sensitivity grade of an interior material used in vehicles according to claim 1, wherein the sensitivity grade is determined such that 1st grade is given when the sensitivity property with the lowest target value achievement level is 99% of the target value achievement level; 2nd grade is given when the sensitivity property with the lowest target value achievement level is from 90% to 99% of the target value achievement level; 3rd grade is given when the sensitivity property with the lowest target value achievement level is from 80% to 90% of the target value achievement level; 4th grade is given when the sensitivity property with the lowest target value achievement level is from 70% to 80% of the target value achievement level: and 5th grade is given when the sensitivity property with the lowest target value achievement level is below 70% of the target value achievement level.

3. The method of evaluating the sensitivity grade of an interior material used in vehicles according to claim 1, wherein the sensitivity properties include color development, color variation, dynamic elongation, permanent compression set and dynamic friction constant.

4. The method of evaluating the sensitivity grade of an interior material used in vehicles according to claim 1, wherein the xenon arc is irradiated with an intensity from 20 to 150 MJ/m$^2$.

* * * * *